United States Patent [19]

Bingham et al.

[11] Patent Number: 5,310,678
[45] Date of Patent: May 10, 1994

[54] NEWCASTLE DISEASE VIRUS GENE CLONES

[75] Inventors: Richard W. Bingham, Liberton, Scotland; Philip Chambers, Newcastle upon Tyne, England; Peter T. Emmerson, Ponteland, England; Neil S. Millar, Sheffield, England

[73] Assignee: National Research Development Corporation, London, England

[21] Appl. No.: 438,945

[22] Filed: Nov. 17, 1989

Related U.S. Application Data

[63] Continuation of Ser. No. 885,765, Jul. 15, 1986, abandoned.

[30] Foreign Application Priority Data

Dec. 18, 1985 [GB] United Kingdom ............... 8531147
Apr. 14, 1986 [GB] United Kingdom ............... 8609037

[51] Int. Cl.$^5$ .................. C12N 1/21; C12N 1/19; C12N 15/45; C12N 15/63
[52] U.S. Cl. .................. 435/252.3; 536/23.72; 435/65.3; 435/172.3; 435/235.1; 435/252.31; 435/252.35; 435/252.33; 435/254.11; 935/12
[58] Field of Search ............ 435/172.3, 320.1, 235.1, 435/239, 254, 5, 69.3, 255, 252.3, 252.31, 252.33, 252.35; 536/27, 23.72; 935/12

[56] References Cited

U.S. PATENT DOCUMENTS

3,429,965  2/1969  Gelenczei ..................... 424/89
4,603,112  7/1986  Paolletti et al. ............... 435/235
4,743,553  5/1988  Rice ........................... 435/252.33

FOREIGN PATENT DOCUMENTS

252060A  1/1988  European Pat. Off. .

OTHER PUBLICATIONS

Purdy, M. A. et al. 1985, Journal of Virology vol. 55 pp. 826-830.
Girard, M. et al. 1985. "Poliovirus cDNA cloned in bacterial plasmids" In *Recombinant DNA Research Viruses*, ed. Y. Becker, Martinus Nijhoff Publishing, Hingham MA, pp. 223-244.
Maniatis, T., et al. (eds.) "Molecular cloning, a Laboratory Manual," Cold Spring Harbor, 1982, pp. 326-328, 374-375.
Sambrook J. et al (eds) "Molecular cloning, a Laboratory Manual," 1989, pp. 8.6, 8.7, 11.12 and 11.13.
van den Elsen, P. et al "Isolation of cDNA clones encoding ... " The Nature 312 413-418 (1984).
Wallis, S. C. et al "The isolation of cDNA clones for human ... ", The EMBO Journal 2 2369-2373 (1983).
Choppin et al "The Function and Inhibition ... " The Jour. of Infectious Disease vol. 143, No. 3, Mar. 1981, pp. 352-363.
Scheid et al "Two Disulfide-Linked ... " Virology 80, 54-66 (1977) pp. 54-66.
Scheid et al "Isolation & Purification ... " Jour. of Virol. Feb. 1973, pp. 263-271.
Avery et al "Use of Antibodies to ... " Infections & Immun. Dec. 1979, pp. 795-801.
Wallace et al "The use of Synthetic ... " Nucleic Acids Res. vol. 4, No. 4 1981.
Jorgensen "Partial Nucleotide ... " Virus Research, Sep. 15-20, 1985, p. 54.
Wallace et al "Hybridization of Synthetic ... " Nucleic Acids Res. No. 11, 1979, pp. 3543-3556.
Suggs et al "Use of Synthetic Oligonucleotides ... " Proc. Natl Acad. Sci. vol. 78, No. 11 pp. 6613-6617.
Woods et al "Isolation of cDNA for ... " Proc. Natl Acad. Sci vol. 79 (Sep. 1982), pp. 5661-5665.
Moriuchi et al "Thy-1 cDNA Sequence ... " Nature, vol. 301(Jan. 6, 1983), pp. 80-82.
Whitehead et al. "Use of a cDNA Clone ... " Proc. Natl Acad. Sci vol. 30, Sep. 1983, pp. 5387-5391.

(List continued on next page.)

Primary Examiner—Richard A. Schwartz
Assistant Examiner—Mary E. Mosher
Attorney, Agent, or Firm—Nixon & Vanderhye

[57] ABSTRACT

Recombinant DNA encoding a polypeptide precursor of the HN or F glycoprotein of Newcastle Disease Virus has been prepared and sequenced.

12 Claims, 6 Drawing Sheets

OTHER PUBLICATIONS

Kajimura et al "Cloning the Heavy Chain . . . " DNA vol. 2, #3 (1983), pp. 175–182.

Seki et al "Isolation of a Genomic . . . Chem. & Molecular Biology of Ia/Dr Antigens Friday Apr. 16, #563 p. 365.

Derynck et al "Human Transforming Growth . . . " Nature, vol. 316 (Aug. 22, 1985), pp. 701–705.

Grantham et al "Codon Catalog Usage . . . " Mucleic Acid Res. vol. 9 #1 1981, pp. 143–175.

Lathe "Synthetic Oligonucleotide . . . " J. Mol. Biol. (1985) 183, 1–12.

Derynck et al "Human Transforming Growth . . . " Cell, vol. 38 (Aug. 1984) 287–297.

Ullrich et al "Human Epidermal Growth . . . " Nature, vol. 309 (May 31, 1984) pp. 418–425.

Ullrich et al "Isolation of the Human Insulin-like . . . " Dept. of Molecular Biology, Genentech Inc, San Francisco, CA pp. 361–364.

Ullrich et al "Human Insulin Receptor . . . " Nature, vol. 313, (Feb. 28, 1985), pp. 756–761.

Pennica et al "Human Tumour Necrosis . . . " Nature vol. 312 Dec. 20/27, 1984, 724–729.

Toole et al "Molecular Cloning of a cDNA . . . " Nature vol. 312 (Nov. 22, 1984), pp. 342–347.

Wood et al "Expression of Active . . . Nature vol. 312 (Nov. 22, 1984), pp. 330–336.

Jaye et al "Isolation of a Human anti-haemophilic . . . " Nucleic Acids Research, vol. 11, No. 8, 1983, pp. 2325–2335.

Docherty et al "Sequence of human tissue . . . " Nature vol. 318 (Nov. 7, 1985), pp. 66–69.

Lauffer et al "Topology of Signal Recognition . . . " Nature vol. 318 Nov. 28, 1985) pp. 334–338.

Carlson "Development and Application of Genetically . . . " Avian Diseases, vol. 30 #1, pp. 24–27.

Lomniczi, B. et al. 1971. *J. Gen. Virol.* vol. 13 pp. 111–119.

Brett, M. A. 1969. *Virology* vol. 38 pp. 485–488.

Suzu, S. et al. 1987. Nucleic Acids Res. vol. 15 pp. 2945–2958.

McGinnes, Wilds and Morrison, Virus Research 7, 187–202 (1987).

"Virus Morphology", 2nd edition, by Madeley and Field, Churchill Livingstone Press (1988), pp. 154, 155, 162 & 163.

Pringle, "Paramyxoviruses and Disease" in "Molecular Basis of Virus Disease" eds. Russel and Almond, Soc. Gen. Microbiol. 51–90 (1987).

Wertz et al., Proc. Natl. Acad. Sci. USA 82, 4075–4079 (1985).

Land et al., Nucleic Acids Research 9, 2251–2256 (1981).

Jorgensen et al., Virology 156, 12–24 (1987).

Elango et al., Nucleic Acids Research 11, 5941–5951 (1983).

Johnson et al., Proc. Natl. Acad. Sci. USA 84, 5625–5629 (1987).

Collins et al., Virology 146, 69–77 (1985).

Binns et al "Prospects for a Novel . . . " Israel Jour. of Vet Med vol. 42, No. 2, 1986, pp. 124–127 w/letter.

Paoletti et al "Construction of Live vaccines . . . " Proc. Natl Acad. Sci USA, vol. 81, Jan. 1984 pp. 193–197.

Smith et al "Infectious Vaccinia . . . " Nature, vol. 302, Apr. 1983, pp. 490–495.

Kieny et al "Expression of Rabies Virus . . . " Nature, vol. 312, 1984, pp. 163–166.

Land, H. et al. 1983, "Synthesis of ds-cDNA involving addition of a CMP tails to allow cloning of 5' terminal mRNA sequences." *Methods Enzymol* vol. 100 pp. 285–292.

Koch, E. M. et al. 1984, "Lifelong persistance of paramyxovirus sendai-6/94 in c129 mice: detection of a latent viral RNA by hybridization with a cloned genomic cDNA probe." *Virology.* vol. 136 pp. 78–88.

Wilde et al (1986) Virus Res. 5:77–95.

Espion et al (1987) Arch. Virol. 95:79–95.

McGinnes et al (1986) Virus Res. 5:343–56.

Gallitelli et al (1985) J Virol Methods 11:141–4.

Miura et al (1985) FEBS Lett. 188:112–116.

Paterson et al (1984) Virology 138:310–323.

Alonso et al (1980) BBRC 95:148–55.

Norrander J. et al; Construction of improved M13 vectors using oligonucleotide detected mutagenesis; Gene 26 pp. 101–106 (1983).

Maniatis, T. et al; Molecular Cloning: A Laboratory Manual; Cold Spring Harbor Laboratory; (1982) pp. 3–4.

R. M. Iorio and M. A. Bratt, J. Virology 48, 440–450 (1983).

(List continued on next page.)

OTHER PUBLICATIONS

Y. Umino et al., Archives of Virology 81, 53–65 (1984).
S. R. Weiss et al., J. Virology 18 316–323 (1976).
P. L. Collins et al., J. Virology 43, 1024–1031 (1982).
P. L. Collins et al., J. Virology 35, 682–693 (1980).
P. L. Collins et al., J. Virology 28, 324–336 (1978).
L. E. Dickens et al., J. Virology 52, 364–369 (1984).
S. W. Hiebert et al., J. Virology 54, 1–6 (1985).
R. G. Paterson et al., Proc. Nat. Acad. Sci. USA 81, 6706–6710 (1984).
C. D. Richardson et al., Virology 105, 205–222 (1980).
A. Wilde et al., J. Virology 51, 71–76 (1984).
B. M. Blumberg et al., J. Virology 66, 317–331 (1985).
B. M. Blumberg et al., Cell 41, 269–278 (1985).
Y. Hidaka et al., Nucleic Acids Research 12, 7965–7973 (1984).
M. Ranki et al., Gene 21, 77–85 (1983).
P. Chambers et al., Abstract for meeting of the Biochemical Society, Oxford England (Jun. 1985).
P. Chambers et al., Poster shown at meeting of the Biochemical Society, Oxford England (Jul. 17, 1985).
P. Chambers et al., J. Gen Virol. 67, 475–486 (1986).
P. Chambers et al., Biochemical Society Transactions 14 (1) 100–101 (1986).
P. L. Collins et al., Proc. Natl. Acad. Sci. USA, 81, 7683–7687 (1984).

```
                    Bam HI                        | M   G   P   R   P
ACGGGTAGAAGATTCTGGATCCCGGTTGGCGCCTTCTAGGTGCAAGATGGGCCCCAGACC
    10        20        30        40        50        60
              F gene coding sequence
  S   T   K   N   P   V   P   M   M   L   T   V   R   V   A   L   V   L   S   C
TTCTACCAAGAACCCAGTACCTATGATGCTGACTGTCCGAGTCGCGCTGGTACTGAGTTG
    70        80        90        100       110       120

I   C   P   A   N   S   I   D   G   R   P   L   A   A   A   G   I   V   V   T
CATCTGTCCGGCAAACTCCATTGATGGCAGGCCTCTTGCGGCTGCAGGAATTGTGGTAAC
    130       140       150       160       170       180

G   D   K   A   V   N   I   Y   T   S   S   Q   T   G   S   I   I   V   K   L
AGGAGACAAAGCAGTCAACATATACACCTCATCCCAGACAGGATCAATCATAGTTAAGCT
    190       200       210       220       230       240

L   P   N   L   P   K   D   K   E   A   C   A   K   A   P   L   D   A   Y   N
CCTCCCAAACCTGCCCAAGGATAAGGAGGCATGTGCGAAAGCCCCCTTGGATGCATACAA
    250       260       270       280       290       300

R   T   L   T   T   L   L   T   P   L   G   D   S   I   R   R   I   Q   E   S
CAGGACATTGACCACTTTGCTCACCCCCCTTGGTGACTCTATCCGTAGGATACAAGAGTC
    310       320       330       340       350       360

V   T   T   S   G   G   R   R   Q   K   R   F   I   G   A   I   I   G   G   V
TGTAACTACATCTGGAGGGAGGAGACAGAAACGCTTTATAGGCGCCATTATTGGCGGTGT
    370       380       390       400       410       420

A   L   G   V   A   T   A   A   Q   I   T   A   A   A   A   L   I   Q   A   K
GGCTCTTGGGGTTGCAACTGCTGCACAAATAACAGCGGCCGCAGCTCTGATACAAGCCAA
    430       440       450       460       470       480

Q   N   A   A   N   I   L   R   L   K   E   S   I   A   A   T   N   E   A   V
ACAAAATGCTGCCAACATCCTCCGACTTAAAGAGAGCATTGCCGCAACCAATGAGGCCGT
    490       500       510       520       530       540

H   E   V   T   D   G   L   S   Q   L   A   V   A   V   G   K   M   Q   Q   F
GCATGAGGTCACTGACGGATTATCGCAACTAGCAGTGGCAGTTGGGAAGATGCAGCAGTT
    550       560       570       580       590       600
```

```
          V  N  D  Q  F  N  K  T  A  Q  E  L  G  C  I  R  I  A  Q  Q
         TGTTAATGACCAATTTAATAAAACAGCTCAGGAATTAGGCTGCATCAGAATTGCACAGCA
            610       620       630       640       650       660
                         Sst I
          V  G  V  E  L  N  L  Y  L  T  E  L  T  T  V  F  G  P  Q  I
         AGTTGGTGTAGAGCTCAACCTGTACCTAACCGAATTGACTACAGTATTCGGACCACAAAT
            670       680       690       700       710       720

T  S  P  A  L  N  K  L  T  I  Q  A  L  Y  N  L  A  G  G  N
         CACTTCACCTGCCTTAAACAAGCTGACTATTCAGGCACTTTACAATCTAGCTGGTGGGAA
            730       740       750       760       770       780

M  D  Y  L  L  T  K  L  G  V  G  N  N  Q  L  S  S  L  I  G
         TATGGATTACTTGTTGACTAAGTTAGGTGTAGGGAACAATCAACTCAGCTCATTAATCGG
            790       800       810       820       830       840

S  G  L  I  T  G  N  P  I  L  Y  D  S  Q  T  Q  L  L  G  I
         TAGCGGCTTAATCACCGGCAACCCTATTCTGTACGACTCACAGACTCAACTCTTGGGTAT
            850       860       870       880       890       900

Q  V  T  L  P  S  V  G  N  L  N  N  M  R  A  T  Y  L  E  T
         ACAGGTAACTCTACCTTCAGTCGGGAACCTAAATAATATGCGTGCCACCTACTTGGAAAC
            910       920       930       940       950       960

L  S  V  S  T  T  R  G  F  A  S  A  L  V  P  K  V  V  T  Q
         CTTATCTGTAAGCACAACCAGGGGATTTGCCTCGGCACTTGTCCCAAAAGTGGTGACACA
            970       980       990      1000      1010      1020

V  G  S  V  I  E  E  L  D  T  S  Y  C  I  E  T  D  L  D  L
         GGTCGGTTCTGTGATAGAAGAACTTGACACCTCATATTGTATAGAAACCGACTTGGATTT
           1030      1040      1050      1060      1070      1080

Y  C  T  R  I  V  T  F  P  M  S  P  G  I  Y  S  C  L  S  G
         ATATTGTACAAGAATAGTAACATTCCCTATGTCCCCTGGTATTTATTCCTGCTTGAGCGG
           1090      1100      1110      1120      1130      1140

N  T  S  A  C  M  Y  S  K  T  E  G  A  L  T  T  P  Y  M  T
         CAATACATCGGCCTGTATGTACTCAAAGACCGAAGGCGCACTCACTACGCCATACATGAC
           1150      1160      1170      1180      1190      1200
                                                              Ava I
          I  K  G  S  V  I  A  N  C  K  M  T  T  C  R  C  V  N  P  P
         TATCAAAGGCTCAGTCATCGCTAACTGCAAGATGACAACATGTAGATGTGTAAACCCCCC
           1210      1220      1230      1240      1250      1260
```

```
       G   I   I   S   Q   N   Y   G   E   A   V   S   L   I   D   K   Q   S   C   N
     GGGTATCATATCGCAAAACTATGGAGAAGCCGTGTCTCTAATAGATAAGCAATCATGCAA
         1270      1280      1290      1300      1310      1320

V   L   S   L   D   G   I   T   L   R   L   S   G   E   F   D   A   T   Y   Q
     TGTTTTATCCTTAGACGGGATAACTTTAAGGCTCAGTGGGGAATTCGATGCAACTTATCA
         1330      1340      1350      1360      1370      1380

K   N   I   S   I   Q   D   S   Q   V   I   I   T   G   N   L   D   I   S   T
     GAAGAATATCTCAATACAAGATTCTCAAGTAATAATAACAGGCAATCTTGATATCTCAAC
         1390      1400      1410      1420      1430      1440

E   L   G   N   V   N   N   S   I   S   N   A   L   N   K   L   E   E   S   N
     TGAGCTTGGGAATGTCAACAACTCGATCAGTAATGCTTTGAATAAGTTAGAGGAAAGCAA
         1450      1460      1470      1480      1490      1500

S   K   L   D   K   V   N   V   K   L   T   S   T   S   A   L   I   T   Y   I
     CAGCAAACTAGACAAAGTCAATGTCAAACTGACCAGCACATCTGCTCTCATTACCTATAT
         1510      1520      1530      1540      1550      1560

SphI
       V   L   T   I   I   S   L   V   F   G   I   L   S   L   V   L   A   C   Y   L
     CGTTTTGACTATCATATCTCTTGTTTTTGGTATACTTAGCCTGGTTCTAGCATGCTACCT
         1570      1580      1590      1600      1610      1620

M   Y   K   Q   K   A   Q   Q   K   T   L   L   W   L   G   N   N   T   L   D
     AATGTATAAGCAAAAGGCGCAACAAAAGACCTTATTATGGCTTGGGAATAATACCCTAGA
         1630      1640      1650      1660      1670      1680

Q   M   R   A   T   T   K   M   *
     TCAGATGAGAGCCACTACAAAAATGTGAACACAGATGAGGAACGAAGGTATCCCTAATAG
         1690      1700      1710      1720      1730      1740

TAATTTGTGTGAAAGTTCTGGTAGTCTGTCAATTCGGAGAGTTTAGAAAAAACTACCGGT
         1750      1760      1770      1780      1790      1800

TGTAGATGACCAAAGGACGATATACGGGTAGAACGGTAAGAGAGGCCGCCCCTCAATTGC
         1810      1820      1830      1840      1850      1860

M   D
     GAGCCGGGCTTCACAACCTCCGTTCTACCGCTTCACCGACAGCAGTCCTCAGTCATGGAC
         1870      1880      1890      1900      1910      1920
```

HN gene coding sequence

```
  R   A   V   S   Q   V   A   L   E   N   D   E   R   E   A   K   N   T   W   R
CGCGCAGTTAGCCAAGTTGCGTTAGAGAATGATGAAAGAGAGGCAAAAAATACATGGCGC
     1930      1940      1950      1960      1970      1980

L   I   F   R   I   A   I   L   L   L   T   V   V   T   L   A   T   S   V   A
TTGATATTCCGGATTGCAATCTTACTCTTAACAGTAGTGACCTTAGCTACATCTGTAGCC
     1990      2000      2010      2020      2030      2040

S   L   V   Y   S   M   G   A   S   T   P   S   D   L   V   G   I   P   T   R
TCCCTTGTATATAGCATGGGGGCTAGCACACCTAGCGACCTTGTAGGCATACCGACCAGG
     2050      2060      2070      2080      2090      2100

I   S   R   A   E   E   K   I   T   S   A   L   G   S   N   Q   D   V   V   D
ATTTCTAGGGCAGAAGAAAAGATTACATCTGCACTTGGTTCCAATCAAGATGTAGTAGAT
     2110      2120      2130      2140      2150      2160

R   I   Y   K   Q   V   A   L   E   S   P   L   A   L   L   N   T   E   T   T
AGGATATATAAGCAAGTGGCCCTTGAGTCTCCGTTGGCATTGTTAAACACTGAGACCACA
     2170      2180      2190      2200      2210      2220

I   M   N   A   I   T   S   L   S   Y   Q   I   N   G   A   A   N   N   S   G
ATTATGAACGCAATAACATCTCTCTCTTATCAGATTAATGGAGCTGCGAACAACAGCGGG
     2230      2240      2250      2260      2270      2280

W   G   A   P   I   H   D   P   D   F   I   G   G   I   G   K   E   L   I   V
TGGGGGGCACCTATCCATGACCCAGATTTTATCGGGGGGATAGGCAAAGAACTCATTGTA
     2290      2300      2310      2320      2330      2340

D   D   A   S   D   V   T   S   F   Y   P   S   A   F   Q   E   H   L   N   F
GATGATGCTAGTGATGTCACATCATTCTATCCCTCTGCATTTCAAGAACATCTGAATTTT
     2350      2360      2370      2380      2390      2400

Nar I
  I   P   A   P   T   T   G   S   G   C   T   R   I   P   S   F   D   M   S   A
ATCCCGGCGCCTACTACAGGATCAGGTTGCACTCGGATACCTTCATTTGACATGAGTGCT
     2410      2420      2430      2440      2450      2460

T   H   Y   C   Y   T   H   N   V   I   L   S   G   C   R   D   H   S   H   S
ACCCATTACTGCTACACTCATAATGTAATATTGTCTGGATGCAGAGATCACTCACACTCA
     2470      2480      2490      2500      2510      2520

H   Q   Y   L   A   L   G   V   L   R   T   T   A   T   G   R   I   F   F   S
CATCAGTATTTAGCACTTGGTGTGCTCCGGACAACTGCAACAGGGAGGATATTCTTTTCT
     2530      2540      2550      2560      2570      2580
```

```
       T  L  R  S  I  S  L  D  D  T  Q  N  R  K  S  C  S  V  S  A
      ACTCTGCGTTCCATCAGTCTGGATGACACCCAAAATCGGAAGTCTTGCAGTGTGAGTGCA
         2590      2600      2610      2620      2630      2640

T  P  L  G  C  D  M  L  C  S  K  V  T  E  T  E  E  E  D  Y
      ACTCCCTTAGGTTGTGATATGCTGTGCTCGAAAGTCACGGAGACAGAGGAAGAAGATTAT
         2650      2660      2670      2680      2690      2700

N  S  A  V  P  T  L  M  A  H  G  R  L  G  F  D  G  Q  Y  H
      AACTCAGCTGTCCCTACGCTGATGGCACATGGGAGGTTAGGGTTCGACGGCCAATACCAC
         2710      2720      2730      2740      2750      2760

E  K  D  L  D  V  T  T  L  F  E  D  W  V  A  N  Y  P  G  V
      GAAAAGGACCTAGACGTCACAACATTATTTGAGGACTGGGTGGCCAACTACCCAGGAGTA
         2770      2780      2790      2800      2810      2820

Acc I
       G  G  G  S  F  I  D  G  R  V  W  F  S  V  Y  G  G  L  K  P
      GGGGGTGGATCTTTTATTGACGGCCGCGTATGGTTCTCAGTCTACGGAGGGCTGAAACCC
         2830      2840      2850      2860      2870      2880

N  S  P  S  D  T  V  Q  E  G  K  Y  V  I  Y  K  R  Y  N  D
      AATTCACCCAGTGACACTGTACAGGAAGGGAAATATGTAATATACAAGCGATACAATGAC
         2890      2900      2910      2920      2930      2940

T  C  P  D  E  Q  D  Y  Q  I  R  M  A  K  S  S  Y  K  P  G
      ACATGCCCAGATGAGCAAGACTACCAGATCCGAATGGCCAAGTCTTCGTATAAGCCCGGG
         2950      2960      2970      2980      2990      3000

R  F  G  G  K  R  I  Q  Q  A  I  L  S  I  K  V  S  T  S  L
      CGGTTTGGTGGGAAACGCATACAGCAGGCTATCTTATCTATCAAGGTGTCAACATCTTTG
         3010      3020      3030      3040      3050      3060

G  E  D  P  V  L  T  V  P  P  N  T  V  T  L  M  G  A  E  G
      GGCGAAGACCCAGTACTGACTGTACCGCCCAACACAGTCACACTCATGGGGGCCGAAGGC
         3070      3080      3090      3100      3110      3120

R  I  L  T  V  G  T  S  H  F  L  Y  Q  R  G  S  S  Y  F  S
      AGAATTCTCACAGTAGGGACATCTCATTTCTTGTATCAGCGAGGGTCATCATACTTCTCT
         3130      3140      3150      3160      3170      3180

P  A  L  L  Y  P  M  T  V  S  N  K  T  A  T  L  H  S  P  Y
      CCCGCGTTATTATATCCTATGACAGTCAGCAACAAAACAGCCACTCTTCATAGTCCCTAT
         3190      3200      3210      3220      3230      3240
```

```
         T  F  N  A  F  T  R  P  G  S  I  P  C  Q  A  S  A  R  C  P
        ACATTCAATGCCTTCACTCGGCCAGGTAGTATCCCTTGCCAGGCTTCAGCAAGATGCCCC
           3250      3260      3270      3280      3290      3300

N  S  C  V  T  G  V  Y  T  D  P  Y  P  L  I  F  Y  R  N  H
        AACTCGTGTGTTACTGGAGTCTATACAGATCCATATCCCCTAATCTTCTATAGGAACCAC
           3310      3320      3330      3340      3350      3360

T  L  R  G  V  F  G  T  M  L  D  S  E  Q  A  R  L  N  P  T
        ACCTTGCGAGGGGTATTCGGGACAATGCTTGATAGTGAACAAGCAAGACTTAATCCTACG
           3370      3380      3390      3400      3410      3420

S  A  V  F  D  S  T  S  R  S  R  I  T  R  V  S  S  S  S  T
        TCTGCAGTATTCGATAGCACATCCCGCAGTCGCATAACTCGAGTGAGTTCAAGCAGCACC
           3430      3440      3450      3460      3470      3480

K  A  A  Y  T  T  S  T  C  F  K  V  V  K  T  N  K  T  Y  C
        AAAGCAGCATACACAACATCAACTTGTTTTAAAGTTGTCAAGACCAATAAGACCTATTGT
           3490      3500      3510      3520      3530      3540

L  S  I  A  E  I  S  N  T  L  F  G  E  F  R  I  V  P  L  L
        CTCAGCATTGCTGAAATATCTAATACTCTCTTCGGAGAATTCAGAATCGTCCCGTTACTA
           3550      3560      3570      3580      3590      3600

V  E  I  L  K  N  D  G  V  R  E  A  R  S  G  *
        GTTGAGATCCTCAAAAATGATGGGGTTAGAGAAGCCAGGTCTGGTTAGTTGAGTCAACTA
           3610      3620      3630      3640      3650      3660

TGAAAGAGCTGGGAAGATGGCATTGTATCACCTATCTTCCGCGACACCAAGAATCAAACT
           3670      3680      3690      3700      3710      3720

SstI
        GAATGCCGGTGCGAGCTCGAATTCCATGTCGCCAGTTGACCACAATCAGCCAGTGCTCAT
           3730      3740      3750      3760      3770      3780

GCGATCAGATCAAGTCTTGTCAATAGTCCCTCGATTAAGAAAAAA
           3790      3800      3810      3820
```

NEWCASTLE DISEASE VIRUS GENE CLONES

This is a continuation of application Ser. No. 06/885,765, filed Jul. 15, 1986, now abandoned.

BACKGROUND OF THE INVENTION

1. Field of the Invention

This invention relates to polynucleotides encoding viral polypeptides associated with the poultry disease known as Newcastle Disease and their preparation by recombinant DNA methods.

2. Description of the Prior Art

Newcastle disease virus (NDV) is a typical paramyxovirus and causes a severe respiratory infection in poultry. This disease is of great economic importance, requiring control by vaccination or quarantine with slaughter of all birds in confirmed outbreaks. The genome of NDV is a single strand of RNA of negative polarity, molecular weight $5.2-5.6 \times 10^6$, or approximately 15,000 bases which is transcribed by a polymerase to produce viral mRNA. The genomic RNA is bound to three proteins in the viral nucleocapsid. These proteins are the nucleocapsid protein NP, the phosphoprotein P, and the large protein L. The nucleocapsid is contained within a lipid envelope derived from host cell plasma membranes on the inner surface of which is a shell of membrane or matrix protein M. On the outer surface of the viral envelope are the two viral glycoproteins, the haemagglutinin-neuraminidase HN, involved in the binding of the virus to host cells and the fusion protein F, involved in fusion with and penetration through the membrane.

The primary translation product of the F gene contains a signal sequence which is presumably removed during or shortly after translation of the polypeptide. Glycosylation of the polypeptide occurs as the polypeptide is translated to result in the precursor glycoprotein $F_o$. The glycoprotein $F_o$ is usually cleaved during processing in vivo to give sub-unit polypeptides $F_2$, $F_1$, which are linked by a disulphide bridge. That is the sub-units $F_1$ and $F_2$ together form a single molecule because they are linked between cysteine residues by the —S—S-bond. The peptide bond cleavage correlates with virulence: $F_o$ of virulent strains is cleaved to $F_1$ and $F_2$ in a wide range of host cells, whereas $F_o$ of avirulent strains, such as LaSota and B1, is cleaved only in a restricted range of host cells. Except where $F_o$ is specifically referred to as such, or the context otherwise requires, the term F used herein includes both F and $F_o$.

The primary translation product of the HN gene is the glycoprotein HN. In two avirulent strains a precursor glycoprotein ($HN_o$) is cleaved to active HN by cleavage of a C-terminal glycopolypeptide. Except where $HN_o$ is specifically referred to as such, or the context otherwise requires, the term HN used herein includes both HN and $HN_o$.

Monoclonal antibodies raised against the NDV HN glycoprotein neutralise NDV infectivity, R. M. Iorio and M. A. Bratt, J. Virology 48, 440-450 (1983). Y. Umino et al., Archives of Virology 81, 53-65 (1984) reported that monospecific antisera to the NDV HN glycoprotein were highly neutralising of haemagglutinin and neuraminidase activity. Antisera to the F glycoprotein inhibited haemolysis and virus-induced cell fusion and the combination of anti-HN and anti-F antisera appeared particularly effective in a plaque reduction assay. Accordingly it would be of interest to prepare, by recombinant DNA methods, artificial DNA or RNA encoding the NDV glycoproteins HN and F. (It is convenient herein to refer to DNA or RNA encoding the NDV proteins, although, strictly, it can encode only the polypeptide precursors thereof which are processed in vivo to glycoproteins). The primary products of NDV transcription in vivo are polyadenylated, capped and methylated mRNAs which are complementary to the genomic RNA and have sedimentation coefficients of 35S, 22S and 18S. The 18S and 35S transcripts code for the six proteins, the 18S RNA coding for proteins NP, P, M, HN, and F and the 35S RNA for the large protein L. The 18S RNA contains five distinct monocistronic poly A-mRNAs, i.e. each codes for one of the five proteins. S. R. Weiss et al, Journal of Virology 18, 316-323 (1976) have shown that these 18S mRNAs have relative molecular masses of 5.0, 5.7, 7.1, 7.4 and $8.5 \times 10^5$.

P. L. Collins et al., Journal of Virology 43, 1024-1031 (1982) have performed in vitro translations and thereby have made assignments of the protein coded for by each mRNA. In ascending order of relative molecular mass they are M, P and proteins of r.m.m. 36K and 33K, NP, unglycosylated F and unglycosylated HN.

No definitive genomic map of NDV exists at present. Maps have been constructed by UV transcriptional mapping, as described by P. L. Collins et al., J. Virology 35, 682-693 (1980) and J. Virology 28, 324-336 (1978). These maps are inconsistent. The last published such paper indicated that the NP gene lies nearest the 3' end, followed by the P gene then the M and F genes in unknown order, followed by the HN gene, all in the 3' half of the genome, and the large L gene nearest the 5' end. However, UV transcriptional mapping is an imprecise technique which is known from work on Sendai virus to have given incorrect results.

Recently, L. E. Dickens et al., J. Virology 52, 364-369 (1984) have compared the gene order in human respiratory syncytial virus (a paramxyovirus) with the rhabdovirus VSV and NDV. The gene order disclosed (3' to 5') is NP, P, M, F, HN and L but it is derived from an unpublished personal communication from another scientist.

The SV5 genes encoding the HN and F proteins have been sequenced. See S. W. Hiebert et al., J. Virology 54, 1-6 (1985) and R. G. Paterson et al., Proc. Nat. Acad. Sci. USA 81, 6706-6710 (1984).

C. D. Richardson et al., Virology 105, 205-222 (1980), sequenced the first 20 amino acids at the N-terminal end of the $F_1$ protein of Sendai Virus, SV5 and NDV. A mixture of all 18-mer oligonucleotides encoding the six consecutive amino acids of this NDV sequence with the lowest number of possible codons would have to contain a minimum of 864 different oligomers.

Recently, A. Wilde et al., Journal of Virology 51, 71-76 (1984) have shown that the 22S NDV RNA transcript gives rise to polycistronic RNA molecules. Their paper reports at page 75, R.H. column, lines 16-19 that cDNA clones derived from individual NDV genes were used to show that the RNA was bi- or tri-cistronic. No further information about such gene clones was given.

The Sendai virus HN and F genes have been sequenced by B. M. Blumberg et al., Journal of Virology 66, 317-331 (1985) and Cell 41, 269-278 (1985). Also Y. Hidaka et al., Nucleic Acids Research 12, 7965-7973 (1984) have sequenced part of the F gene.

3. The inventors' own prior disclosures

The present inventors have been engaged in cloning NDV genes by recombinant DNA technology. On Jan. 10th, 1985 at a Society for General Microbiology workshop at Birmingham, England, they presented orally an outline of their work including a short region of cDNA sequence thought to be in the region of the junction between HN and L genes. An open reading frame was not given.

On Jul. 17th, 1985, they gave an oral paper, with overhead projection, to a meeting of the Biochemical Society at Oxford, England. A brief abstract outlining the work but giving no detail, was circulated to delegates in about June 1985. A poster was exhibited in July 17th at the meeting. The poster reported the cloning in the plasmid pBR322 of a series of overlapping small fragments which by laborious and careful mapping techniques had been shown to span the entirety of the F and HN genes. The poster gave no nucleotide sequence information in the coding region but reported a deduced 69-residue amino acid sequence NPTSAVFD . . . PLLVEILKN near the 5' end of the HN gene. This sequence did not include any methionine or tryptophan residues which have unique DNA codons. The oral paper went no further in content than to the poster.

Despite the above reports, it was still impossible to specify with confidence the location on the NDV genome of the HN and F genes particularly in view of the unreliability of UV transcriptional mapping. Nor was there published any nucleotide sequence information which would enable the man skilled in the art to construct a small number of probes whereby the relevant genes in an NDV gene library could be hybridised to the probe and thence extracted from the library. Further, no such NDV gene library was known at the priority date of this patent application. Accordingly it remained a problem to prepare a cDNA or RNA coding for the HN and F genes of NDV.

SUMMARY OF THE INVENTION

The present invention provides polynucleotides, especially DNA, encoding part or all of the HN and F polypeptides of Newcastle Disease Virus RNA. Whereas the genome of NDV is of length approximately 15,000 nucleotides, it has been determined, by this invention, that the portion thereof coding for the F polypeptide is approximately 1,660 nucleotides long and that coding for the HN polypeptide approximately 1,730 nucleotides long. These HN- and F-coding portions of the genome are believed to be those which give rise to immunity-stimulating polypeptides. The invention herein is seen as providing relatively short lengths of polynucleotide which correspond to or are complementary to these genes, but not for substantial elements within the remainder of the genome. Thus, it is envisaged that the polynucleotides herein will not include substantial lengths of additional sequence corresponding to or complementary to other parts of the NDV genome. On the other hand, the invention is not to be construed to such HN- and F-gene polynucleotides as to exclude a polynucleotide which encompasses short lengths of additional NDV gene sequence, for example n nucleotides at either or both ends of the F and/or HN gene, where n is a number from (say) 1 to 200, especially 1 to 50. Note that signal sequences are included within the definition of the polynucleotide as corresponding to or complementary to the HN- and F-gene. The "additional gene sequence" means sequence from another NDV gene, rather than merely parts of the HN- and F-sequence involved in processing the RNA to give the HN- and F-genes and which do not encode the respective polypeptides.

It is known that the proteins HN and F are glycoproteins. The polynucleotides of the invention encode the polypeptide portion thereof, i.e. that portion which is subsequently to be glycosylated in vivo.

The F polypeptide is also processed in vivo by cleavage into the two shorter polypeptides $F_1$, $F_2$. Accordingly, the invention encompasses a polynucleotide encoding $F_1$ and $F_2$ polypeptides as separate molecules or disulphide bridged as a single molecule or their bioprecursor F polypeptide. It is generally accepted that virion RNA or DNA contains portions which are more directly relevant to stimulation in vivo of immunity than other portions. These epitopes can be quite small. For example in foot and mouth disease virus, the most antigenic region of the $VP_1$ polypeptide lies between amino acids 140–160 of a 210-amino acid long chain. A relatively short polypeptide of FMDV encoded by this region has been reported to stimulate immunity to the disease in cattle.

According to an important aspect of the invention, therefore, there is provided an artificial polynucleotide (1) encoding an HN and/or F polypeptide of NDV RNA, a bioprecursor of a said polypeptide or an epitopic portion of said polypeptide or an artificial polynucleotide (2) complementary to polynucleotide (1).

The term "polynucleotide" includes single-stranded (ss) and double-stranded (ds) DNA, RNA and chemically or biosynthesised nucleotide polymers of varying lengths from 16 nucleotides also upwards. Also within the invention are polynucleotides labelled for identification purposes, especially labelled as ss probes. The term "artificial" as used herein signifies the intervention of man, by any means, in the production of the polynucleotide. In addition to artificial polynucleotides per se, the invention includes, of course, recombinant molecules. These can be broadly defined as consisting of vector polynucleotide and polynucleotide foreign thereto, the foreign polynucleotide consisting of or including a polynucleotide of the invention as defined above. Normally the polynucleotide is DNA and the invention includes particularly DNA wherein the vector is a cloning vehicle or expression vector. The expression vector can be, for example, a prokaryotic cell expression vector or a eukaryotic cell expression vector, such as fowl pox virus DNA. The term "vector" herein also includes shuttle vectors. Where expression is required, the polynucleotide will additionally contain a signal sequence of the kind effective for translation and other processing of the mRNA into the desired HN and/or F proteins.

The invention includes, further, a host cell containing or infected with recombinant polynucleotides as defined above.

A primary use of the polynucleotides of the invention encoding part of the HN and/or F polypeptides is in the preparation of labelled probes which can be used for diagnosis of the presence of Newcastle Disease Virus in a sample taken from poultry. In other words the probes are used in an assay, whereby a positive signal from an attempted hybridisation will indicate the presence of the virion RNA in the sample and therefore presence of Newcastle Disease Virus.

A second use of the polynucleotides of the invention is as intermediates in the production of polypeptides by recombinant DNA technology. It is contemplated, therefore, that an expression vector of the invention containing a strong promoter, cloned in, for example, *E. coli* will give rise to the appropriate encoded polypeptides.

BRIEF DESCRIPTION OF THE DRAWING

The FIGURE shows the nucleotide sequence of cDNA coding for NDV F and HN genes.

DESCRIPTION OF THE PREFERRED EMBODIMENTS

The genome of NDV is a negative-stranded RNA, i.e. the strand which actually encodes the proteins is its complement. In in vivo processing, the complement is the mRNA. The present invention includes cDNA which is complementary to the genome and therefore corresponds to the mRNA in being a coding strand. The invention includes, of course, such cDNA as a single strand and a DNA duplex of such a strand and its complementary DNA, that complementary DNA therefore being an anti-coding strand corresponding to the genome. The strain of Newcastle Disease Virus used in the recombinant DNA work which has led to the present invention is Beaudette C. This strain is quite widely available and in the present instance was obtained originally from Professor C. F. Fox, University of California, Los Angeles, U.S.A. It is available from the Government-funded Central Veterinary Laboratory, Weybridge, Surrey KT15 3NB, U.K., which acts as an international reference laboratory for NDV.

The invention includes specifically polynucleotides as aforesaid derived from Beaudette C strain. Immunological studies indicate the the variation between different strains of NDV is not great and is likely to be substantially less than the difference between NDV and other paramyxoviruses such as Sendai Virus and SV5. Nucleotide sequences for the F and HN genes of Beaudette C strain are shown hereinafter in the Example.

With the aid of the sequence information provided by the present invention, it is contemplated that those skilled in the art will be able to "take a short cut" to obtaining cDNA to the RNA of Beaudette C or to other strains of NDV or another paramyxovirus or its complement. This can be done, for example, by chemical synthesis of oligonucleotides of sufficient length to have a reasonable chance of being unique to the HN- and/or F coding region of NDV Beaudette C strain. Such oligonucleotides will ordinarily have a minimum length of 12–18 nucleotides, the exact minimum number being a function of the degree of certainty to be assigned to there being no other identical or near-identical sequence elsewhere in the NDV genome. A probe of the ss nucleotide is then constructed and used to probe the viral RNA or the gene library of cDNA complementary thereto of the same or different strain of NDV. Other paramyxoviruses having a high degree of homology with NDV, notably avian paramyxoviruses, could be employed analogously. An example of such a paramyxovirus is Avian Paramyxovirus virus 3 which causes egg drop syndrome. Conveniently a cDNA library is used and by colony hybridisation it is then possible to detect which clones contain DNA complementary to HN or F Beaudette C gene. If necessary, appropriate restriction enzymes can then be used for sub-cloning of the relevant genes. It will be appreciated that in such a gene extraction method, it is a relatively simple matter, if necessary by trial and error, to locate a sequence of at least, say, 18 nucleotides in length which will serve as such a probe. Accordingly, the invention provides specifically an artificial polynucleotide (1) encoding the HN and/or F polypeptide of Newcastle Disease Virus RNA Beaudette C strain, a bioprecursor of said polypeptide or an epitopic portion of said polypeptide, an artificial polynucleotide (2) complementary to polynucleotide (1), an artificial polynucleotide (3) encoding a corresponding polypeptide of a paramyxovirus of overall nucleotide homology of at least 80% with the HN and/or F-coding gene respectively of Newcastle Disease Virus Beaudette C strain and obtainable via hybridisation from a library of genes of said paramyxovirus or their complement or an artificial polynucleotide (4) complementary to polynucleotide (3).

There are a large number of strains of NDV to which the above technique can be applied. Some of the better known ones are strains AV, LK, N(La Sota), HP-16, Texas, Herts, F, Queensland, Ulster 2C and Hitchner B1. Hitchner B1 in particular, is a well known strain, described, for example by P. Chambers et al., J. General Virology 58, 1–12 (1982). Hitchner B1 is obtainable from the Central Veterinary Laboratory referred to above.

Overall homology of the HN and/or F gene, as recited above, is useful as an indicator of the kinds of other paramyxovirus covered by the definition. It does not cover Sendai Virus or SV5.

Epitopes and the polypeptides can be located by sequencing cDNA of variants of the Beaudette C strain of NDV selected on the basis of resistance to monoclonal antibodies to an HN or F polypeptide. Regions where amino acid sequence changes are clustered will indicate the position of the epitopes. Some degree of prediction or confirmation can be obtained from a study of the amino acids encoded, it being generally reckoned that the epitopic region should be relatively rich in hydrophilic amino acids such as arginine (R), lysine (K), aspartic acid (D), glutamic acid (E), asparagine (N) and glutamine (Q). Having thus determined the epitopic regions, it is then possible to synthesise a polypeptide or a DNA oligonucleotide which encodes a polypeptide for those regions. The synthesis can be done chemically or by the use of an appropriate combination of restriction enzymes on a longer length of DNA obtained by recombinant DNA methods such as those described herein.

Polynucleotides of the invention comprising part only of an HN and/or F-gene coding sequence are useful for hybridisation purposes, e.g. diagnostically or in a process of obtaining nucleic acids of a related virus or viral strain. In order to ensure successful hybridisation of the polynucleotides of the invention to RNA or cDNA of another paramyxovirus or another NDV strain, the degree of homology in terms of nucleotide sequence in the hybridisation should ordinarily be not less than 85% and preferably at least 90%, most preferably 90% or higher. Such a degree of homology, however, need apply only to the particular length of sequence which is to be hybridised, for example of minimum length 12–18 nucleotides long. It is not necessary that such a degree of homology apply over the entire molecule, although, of course, the longer the oligonucleotide or polynucleotide selected for the hybridisation and the greater its homology, the higher the stringency of hybridisation and therefore certainty of achieving the desired result is likely to be. It is expected, however, that an overall degree of homology of at least 80% or of the order indicated above will ordinarily be applicable over the entire HN or F gene sequence taken as a whole. If the sequence chosen is very short, the degree of homology should be correspondingly very high, for example 95–100% over a sequence of length as short as 12 nucleotides, and 85% or more, preferably 90% or more, over a sequence of length at least 16 nucleotides. Minimum probe lengths and degrees of homology with the paramyxovirus are preferably adjusted accordingly.

cDNA of the present invention has been prepared by methods well known in themselves, comprising transcribing the genomic RNA with an appropriate enzyme to yield a RNA:DNA hybrid, dC-tailing the hybrids, annealing them to dG-tailed restricted plasmid vector, whereby the hybrid is incorporated in the vector, and using the plasmid vector to transform a bacterial host. Relevant clones were selected by antibiotic sensitivity and resistance, in the usual way, and further verified by colony hybridisation to a probe of separately prepared NDV cDNA. The ingenuity of the method employed lies really in the mapping technique and overcoming the difficulty that it was not possible unambiguously to hybridise sub-clones of recombinant DNA to RNA of the F gene. The NP and F genes have very similar relative molecular masses, making it difficult to perform an adequate separation of their mRNA by electrophoresis. By an ingenious combination of various methods, however, it was possible unambiguously to assign the various clones produced to the correct genes.

The cDNA prepared according to Example 1 hereinafter takes the form of a series of clones of length approximately 700–1400 nucleotides, appropriate portions of DNA inserts of which are ligated together, so as to produce DNA complementary to the full length or nearly the full length genes. The plasmid inserts can be ligated together using well known methods, for example by restricting the DNA insert of a first clone with a restriction enzyme which cuts it uniquely at its 5' end. This first DNA insert is to be ligated to a second DNA insert which is 5' wards of the first. The second DNA insert is restricted by the same enzyme at a position near its 3' end. The two inserts can then be ligated in a well known manner, which can be sticky-ended or blunt-ended according to the kind of restriction enzyme used. A third insert can be ligated onto the two now-ligated inserts in a similar fashion, if necessary, and the resulting recombinant molecule ligated into an appropriate vector.

The term "artificial" used herein in relation to the polynucleotides was defined above to denote that it is a man-made polynucleotide as distinct from one found in nature. The term implies no limitation on the method of manufacture, which can be chemically or by a biological means involving intervention of man. Conventionally, polynucleotides are of DNA, but it is also possible to make them of RNA by use of appropriate transcription enzymes. RNA inserts can be introduced into DNA vectors. Any of the conventional cloning vectors can be used for cloning, preferably those having a multicopy facility such as pBR322, other col.E1-based plasmids and M13 vectors. The vector should obviously be compatible with the host, pBR322 being compatible with the conventional E. coli host.

For expression of the HN and F proteins, any of the usual expression vectors, especially bacterial vectors, containing a strong promotor and appropriate to the desired host can be used. Particularly preferred such expression vectors are those containing a strong promotor sequence, for example a phage lambda vector containing the $P_L$ (leftward promoter of Phage lambda), or a plasmid containing the lac or gal promotor which switches on a beta-lactamase or beta-galactosidase gene and which can be linked to the HN or F NDV gene encoded by polynucleotide of the invention. The so-called promiscuous plasmids such as RP4 or others of the Inc (incompatibility) -P1 group of plasmids can be used.

The usable bacterial hosts for the vectors include any of the conventional bacterial hosts such as *E. coli, B. subtilis* or *Streptomyces* spp. Cloning in lower eukaryotes such as yeast, which is gaining in popularity, can be practised by use of a suitable shuttle vector, whereby the insert DNA in the vector can be shuttled from *E. coli* to a yeast, for example.

As examples of an appropriate shuttle vector, the plasmids $YR_p7$ and pJDB219 are mentioned as vectors able to replicate in *E. coli* and in the yeast organism *Saccharomyces cerevisiae*.

It is also contemplated that the polynucleotides of the invention will have value for introduction into a eukaryotic vector such as DNA of an attenuated strain of fowl pox virus.

The polynucleotides of the invention are useful for preparing a probe, i.e. a labelled polynucleotide, either for the purposes of extracting similar genes from a gene library or for identifying the presence of NDV virions in a sample obtained from poultry, as mentioned above. For this purpose, the polynucleotide can be labelled in any of the well known ways, e.g. by a radioactive isotope, preferably with $^{32}P$, enzyme labelling by the method of D. C. Ward et al., European patent specification 63879A (Yale University) or of A. D. B. Malcolm et al., PCT patent specification WO84/03250 or fluorescently. The probe polynucleotide will normally take a single-stranded form and preferably be ss DNA.

The method of assay used in diagnosis will conveniently be sandwich hybridisation as described by M. Ranki et al., Gene 21, 77–85 (1983) whereby the labelled probe can hybridise to one portion of an NDV-specific RNA, for example the HN or F mRNA, which may be present in the sample under investigation. Immobilised ssDNA or RNA which can hybridise to another portion of the same NDV-specific RNA molecule forms the other diagnostic reagent. Successful hybridisation takes place at two sites on the NDV-specific RNA if present in the sample, whereby the NDV-specific RNA is hybridised to (or "sandwiched between") both diagnostic reagents, and attachment of label to the insolubilised material denotes a positive result in the assay. Other forms of assay relying on DNA-DNA, DNA-RNA or RNA-RNA hybridisation are well known in the art and can be employed in the context of the present invention.

The following Example illustrates the recombinant DNA techniques employed in obtaining bacterial clones containing plasmids having inserts of HN- and/or F- coding cDNA for NDV genomic RNA and the correct or substantially correct sequences of the cDNA encoding the F and HN genes of Beaudette C Virus NDV RNA.

EXAMPLE

Materials

NDV strain Beaudette C was obtained from Professor C. F. Fox, University of California, Los Angeles. NDV strain Hitchner B1 was obtained from J. B. McFerran, Veterinary Research Laboratories. Stormont, UK. Madin and Darby bovine kidney (MDBK)

cells were obtained from Flow Laboratories, Irvine, UK. *E. coli* strain DH1 was obtained from Peter Meacock, University of Leicester, UK. Reverse transcriptase was from Life Sciences Inc., Florida, USA. Random hexanucleotide primer mixture generated by DNase digestion of calf thymus DNA and terminal transferase were from Pharmacia, Milton Keynes, UK. Radionucleotides were from Amersham International, Amersham, UK. DNase 1 was from Sigma, London, UK. DNA polymerase and Klenow fragment were from BCL, Lewes, UK. Nitrocellulose filters were from Millipore, Molsheim, France or from Amersham International, UK. Polynucleotide kinase, vanadyl ribonucleoside complexes and oligo dG-tailed PstI-cut pBR322 were from BRL, Cambridge, UK. Restriction endonucleases were from BRL, BCL, or NBL enzymes, Cramlington, UK. Pall Biodyne A membranes were obtained from Pall Process Filtration Ltd., Portsmouth, UK.

Molecular cloning of NDV

The cloning procedure was modified from A. J. Cann et al., Nucleic Acids Research 11, 1267–1281 (1983). NDV strain Beaudette C was grown in eggs and purified by centrifugation by the procedure of P. Chambers et al., Journal of General Virology 50, 155–166 (1980). RNA was extracted by digestion of NDV (approximately 5 mg protein) with 2 mg protease K in a buffer containing 10 mM vanadyl ribonucleoside complexes, 0.15M NaCl, 1% SDS, 12 mM EDTA, 0.1M Tris/HCl pH 7.5, at 37° C. for 1 hour, followed by three extractions at 56° C. with phenol/0.1% (w/v) 8-hydroxyquinoline. Virion RNA was concentrated into a final volume of 100 microliters $H_2O$ by ethanol precipitation.

Complementary DNA (cDNA) synthesis was performed on 1–2 micrograms virion RNA with 2 micrograms random hexanucleotide primer and 20 units reverse transcriptase in a buffer containing 100 mM NaCl, 8 mM $MgCl_2$, 20 mM 2-mercaptoethanol, 1 microCurie deoxycytidine triphosphate, 50 micromolar deoxynucleoside triphosphates, 50 mM Tris/HCl pH 8.3 for 30 minutes at 37° C., then 90 minutes at 42° C.

RNA: DNA hybrids were desalted in a 2 ml "Sephadex" G100 column, ethanol precipitated, and resuspended in a final volume of 10 microliters $H_2O$. RNA:DNA hybrids were tailed with oligo dC by incubation for 20 minutes at 37° C. with 10 units terminal transferase in a buffer containing 140 mM potassium cacodylate pH 6.9, 1 mM $CoCl_2$, 25 micromolar deoxycytidine triphosphate and 1 microCurie of $^3H$ deoxycytidine triphosphate (a far higher proportion of radionucleotide was incorporated in this second synthetic reaction). Oligo dC-tailed RNA:DNA hybrids were run through a 2 ml "Sephadex" column in annealing buffer (100 mM NaCl, 0.1 mM EDTA, 10 mM Tris/HCl, pH 7.5). 100 Microliters oligo dC-tailed RNA:DNA hybrids in annealing buffer were annealed to 1 microliter (0.25 microgram) oligo dG-tailed PstI-cut pBR322 at 65° C. for 5 minutes, then 45° C. for 2 hours, cooled to room temperature overnight then kept on ice for a further 24 hours (these optimal proportions of hybrid:pBR322 were determined by small scale annealings and transformations). The annealed mixture was transformed into competent *E. coli* strain DH1 and plated onto agar containing 10 micrograms of tetracycline per ml.

The PstI site of pBR322 is within the ampicillin resistance gene. More than 75% of the transformants were ampicillin-sensitive and therefore presumably contained inserts at the PstI site. Transformants that grew up in 2 days at 37° C. were streaked onto nitrocellulose filters on agar plates, grown up, lysed by the method of M. Grunstein and D. S. Hogness. Proc. Nat. Acad. Sci. USA 72, 3961–3965 (1975) and baked. Transformants containing NDV-specific inserts were detected by colony hybridisation on the filters. The NDV gene probe was made as follows. NDV genomic RNA was reverse transcribed in a similar manner to that described above, except that nonradioactive deoxyadenosine triphosphate and $^3H$ deoxycytidine triphosphate were omitted and 20 micro-Curies ($\alpha$-$^{35}S$) deoxyadenosine triphosphate were included. 20–30% of the radioisotope was incorporated into cDNA in a typical reaction. The cDNA was separated from the RNA by boiling. The resultant labelled ss DNA was used as the probe. Filters were prehybridised for 3 hours at 65° C. in a solution containing 5× Denhardt's solution, 6× SSC (0.9M NaCl, 90 mM Na citrate), 50 micrograms/ml boiled sheared calf thymus DNA, then hybridised to probe overnight at 65° C. in a similar solution. Filters were washed three times for 1 hour at 65° C. in 3× SSC/0.1% SDS, dried, then exposed to X-ray film (Kodak NS 59T) at −70° C. A bank of 700 NDV-specific clones was constructed in two stages. The first 300 clones were analysed before the remaining clones were produced. Most of the inserts were in the range 500–1,000 base pairs, although a few inserts were larger than 2,000 base pairs.

Construction of a map of cloned inserts

Four techniques were used to map the cloned inserts with respect to each other and to their positions in the NDV genome.

1. Dot blot hybridisation

Twenty-seven clones out of the first 300 prepared were selected for study based on their high intensity of hybridisation to $\alpha^{35}S$ labelled cDNA and on their large insert sizes (typically 1,000–2,000 base pairs) which were estimated from small scale plasmid preparations (known as "minipreps"). Larger scale plasmid isolations were then performed and plasmid DNA's were linearised with HindIII, boiled to separate the DNA strands, made up to 2× SSPE (0.36M NaCl, 2 mM EDTA, 20 mM $NaH_2PO_4$ pH 8.3) and dotted onto nitrocellulose filters in a known pattern, then baked under vacuum at 80° C. for 2 hours to bind DNA to nitrocellulose. The pattern of DNA dots was probed with a preparation of insert cDNA which was cut out by PstI from a particular plasmid, for example that designated "2.87", purified on an agarose gel followed by electroelution and phenol extractions, see M. S. McDonnell et al., J. Mol Biol. 110 119–146 (1977), and then labelled by nick translation with ($\alpha^{35}S$) deoxyadenosine triphosphate. Hybridisation conditions, washing and exposure to X-ray film were identical to those described above for the screening of transformants. Ten plasmids (including 2.87 itself) hybridised strongly to the probe.

2. Northern blot hybridisation

Selected plasmids were mapped to their corresponding mRNAs by Northern blot hybridisation. MDBK cells were infected with NDV strain Hitchner B1 at 1000 $EID_{50}/90$ mm Petri dish. ($EID_{50}$ =that dose of NDV which has a 50% probability of infecting an egg.) Twenty-four hours post-infection, cell monolayers were rinsed with PBS (137 mM NaCl, 8.1 mM $Na_2HPO_4$, 2.7 mM KCl, 1.5 mM $KH_2PO_4$), then lysed with 4.2M guanidinium thiocyanate, 0.5% sarkosyl L, 25 mM Na citrate, 0.33% Sigma antifoam A pH 7.0. The cell lysate was laid over a cushion of 5.7M caesium chloride in 25 mM Na acetate pH 5.0 and centrifuged overnight to pellet total cellular RNA at 35,000 rpm in a MSE 6×15 ml rotor. The pelleted RNA was resuspended in 5 mM EDTA, 1% SDS, 10 mM Tris/HCl pH 7.4, extracted with 4:1 v/v chloroform:butanol and precipitated at −20° C. after the addition of 0.1 volume 3M Na acetate pH 5.5 and 2.2 volumes ethanol. A control preparation was made from uninfected cells. The RNA was then denatured with 50% formamide, 10% formaldehyde at 60° C. for 5 minutes and electrophoresed on a 1.8% agarose gel containing 6.5% formaldehyde and 20 mM Na phosphate buffer pH 7.0, to yield individual mRNAs. Individual NDV mRNAs are resolved by gel electrophoresis on the basis of their relative molecular masses and the protein coding assignments of these mRNAs have been determined by in vitro translation, Collins et al., supra. Alternate lanes were loaded with infected and uninfected cellular RNA (10 micrograms/track) arranged so that, after blotting, filters could be cut into strips with one track of each of infected and uninfected material per strip. RNA was transferred onto Pall Biodyne A membranes without any staining or pretreatment of the gel, in the manner described by P. S. Thomas, Proc. Nat. Acad Sci. USA 77, 5201–5205 (1980). From each batch of strips, one was probed with viral genomic RNA, hydrolysed with alkali and end-labelled with ($\gamma^{32}$P) adenosine triphosphate by polynucleotide kinase. This was the control to show all the mRNA bands. The other strips were individually probed with the selected appropriate plasmid DNA labelled with ($\alpha^{32}$P) deoxycytidine triphosphate by nick translation. Conditions for hybridisation were based on the method of P. S. Thomas (1980) supra. Filters were prehybridised by incubation for 4–6 hours at 42° C. in 50% deionised formamide, 2.5× Denhardt's solution, 2× SSPE, 0.375% SDS, 250 micrograms/ml boiled salmon sperm DNA. Hybridisation was carried out overnight (18–20 hours) at the same temperature in a similar solution containing the probe. Filters were washed four times for 15 minutes at room temperature in 2× SSC, 0.1% SDS, and once for 15 minutes at room temperature in 1× SET (150 mM NaCl, 2 mM EDTA, 30 mM Tris/HCl pH 8.0) and then twice for 20 minutes at 68° C. in 1× SET or 0.5× SET. The damp filters were sealed in thin polyethylene bags and exposed to X-ray film (Kodak X-Omat S) at room temperature.

3. Restriction enzyme mapping

Plasmids that overlapped, as determined by dot blot hybridisation, were mapped by digestion with a panel of restriction enzymes. In the first instance, PstI, EcoRI, HindIII, BamHI, PvuII and AvaI sites were mapped in cloned inserts, and in many cases this provided sufficient data to align inserts with respect to each other. Where necessary, additional restriction enzyme sites were mapped to confirm overlaps suggested by dot blot hybridisation.

4. Colony hybridisation

The bank of NDV-specific clones was probed with nick translated ($\alpha^{35}$S) labelled insert cDNA to find clones that extended the regions mapped in the initial dot-blot hybridisations. Clones were streaked onto nitrocellulose, grown up on agar overnight at 37° C., lysed and baked as in molecular cloning of NDV above, then hybridised to the probe, washed and dried as for dot blot hybridisation described above. Any clones that hybridised to the probe were analysed to determine the size of the insert in the plasmid. In promising cases, larger scale plasmid preparations were performed and restriction enzyme sites were mapped to determine whether the newly selected plasmids extended the regions present in the probe insert. By the dot blot hybridisation technique (1) above, 22 out of 27 plasmids were mapped into two non-overlapping groups by means of dot blot hybridisations, 10 being strongly hybridised to plasmid 2.87. The others gave only faint non-reproducible spots. The Northern blotting (2, above) made it possible to deduce which genes are represented in a particular plasmid by the mRNAs to which it hybridises, with one important proviso. The proviso was that the NP and F mRNAs were not well resolved and so a plasmid that hybridised to those mRNAs could not be assigned to the NP or F genes on these data alone. The essential results from 8 plasmids interpreted solely on the basis of the Northern blotting are shown in simplified form in Table 1 below. "Yes" indicates strong hybridisation to at least part of the specified gene. Plasmid 2.87 is one of those two above-mentioned non-overlapping groups of plasmids segregated by the dot hybridisation and was found to be located in the L gene.

TABLE 1

| NDV genes | Hybridisation of Plasmids to NDV MRNA coding for specified genes Plasmid designations | | | | | | | |
|---|---|---|---|---|---|---|---|---|
| | 2.87 | 3.73 | 2.73 | 3.01 | 4.77 | 4.26 | 3.48 | 3.93 |
| L | Yes | Yes | | | | | | |
| HN | | Yes | Yes | | | | | |
| NP or F | | | | Yes | Yes | | | |
| P | | | | | | Yes | Yes | |
| M | | | | | | | Yes | Yes |

Clones to fill gaps between the regions mapped in dot blot and Northern blot hybridisations were selected by colony hybridisation. For example, plasmid 2.73 was mapped to the HN gene in the Northern blot hybridisation. Restriction enzyme mapping indicated that it was the furthest 3'- wards of the second group of non-overlapping plasmids segregated by dot blot hybridisation. When the insert from 2.73 was used to probe the colony bank, clone 4.68 amongst others showed a positive hybridisation. Restriction enzyme mapping showed that the insert from 4.68 extended still further 3'-wards into the HN gene.

Only by thus extending the series of plasmid DNA inserts to "fill in" between the M gene and the L gene was it possible to deduce the correct order of the F and HN genes. Plasmids 3.01 and 4.77 (Table 1) were then assigned to the F and NP genes respectively. By means of these types of experiment, a map of NDV-specific cloned inserts was drawn up and the order of the gene-coding regions of the genomic RNA was deduced as (3') NP P M F HN L (5'). It is assumed that NP is at the 3' terminus, because (1) hybridisation of the clones to bicistronic NDV transcripts suggests that NP-P, P-M and M-F transcripts occur and (2) there was a low abundance of clones in NP, an observation in agreement with the finding by A. J. Cann et al., Nucleic Acids Research 11, 1267–1281 (1983) of a low abundance of clones at the 3'- end of the genomic RNA of poliovirus type 3, using a similar cloning protocol.

DNA sequencing

Two clones 1.13 and 3.73 from the second dot hybridisation group provided overlapping cDNA and both contain the junction between the HN and L genes of NDV. These clones were the first to be selected for DNA sequence analysis, with emphasis on the region of overlap. DNA was sub-cloned into the vectors M13 mp8 mp9, mp18 and mp19, using restriction enzyme sites mapped in the cDNA inserts to 'force-clone' fragments. Similar methods were subsequently used on overlapping cDNA extended 3'-wards from the HN-L gene junction through the HN gene and the F gene.

DNA sequence analysis was performed by the dideoxy technique using a universal primer and ($\alpha^{35}S$) deoxyadenosine triphosphate as label. The nucleotide sequence was determined on thin polyacrylamide buffer gradient gels using Fuji X-ray film. Sequencing data was stored, assembled and analysed to give a consensus sequence. In the figure are shown the sequences for cDNA (coding strand) encoding the F and HN genes. The sequence shown, being complementary to the genomic RNA, is in the 5' to 3' direction as is conventional. The F gene is thought to extend from nucleotides 1-1792, there follows an intergenic region and then the HN gene extends from nucleotides 1795-3825.

Referring first to the F gene cDNA and proceeding in the 5' to 3' direction, the $F_o$-coding region is though to extend from the proposed ATG start codon at nucleotides 47-49 to a TGA stop codon at 1706-1708. The cDNA encodes the $F_o$ polypeptide which is cleaved in vivo to $F_2$, $F_1$ ($F_2$ being to the 5'-end of the $F_o$ gene cDNA, $F_1$ to the 3'-end). Cleavage occurs at the C-terminal side of the arginine encoded by nucleotides 392-394. The amino acid sequence after the proposed cleavage site, viz that encoded by nucleotides 395-454, is the same as that of the 20 amino acids at the N-terminal of $F_1$ determined by C. D. Richardson et al., supra. Beyond the end of the $F_1$-coding sequence is a non-coding portion corresponding to the 3' end of the mRNA which then terminates in a poly-A sequence at nucleotides 1787-1792.

The DNA sequence shows five significant potential asparagine-linked glycosylation sites in $F_o$, one (NRT) in $F_2$ at 299-307 and four (NKT, NTS, NIS and NNS) in $F_1$ at 617-625, 1142-1150, 1385-1393 and 1457-1465. The NNT site near the C-end of $F_1$ is considered insignificant since it lies in the region of the protein which does not cross the membrane.

The amino acid sequence of the HN polypeptide gene is shown with an ATG start codon at nucleotides 1915-1917 and a TAG stop codon at nucleotides 3646-3648; this is followed by a 177-nucleotide non-coding region which terminates in a poly-A sequence at the 3' end of the mRNA. The DNA sequence shows six potential glycosylation sites in HN, (NNS, NDT, NKT, NHT, NPT, NKT) at 2269-2277, 2935-2943, 3211-3219, 3355-3363, 3412-3420 and 3526-3534.

The non-coding region contains encodes a potential glycosylation site (NQT) at 3712-3720 and has a further TGA stop codon at 3757-3759, near the 3' end of the mRNA, which may provide an explanation for the origin of $HN_o$ in certain strains of NDV.

The HN proteins of the NDV strains Ulster and Queensland are known to be synthesised in a precursor form ($HN_o$) which is cleaved to active HN by the removal of a C-terminal glycopeptide. These considerations suggest that the gene encoding the $HN_o$ precursor for the HN protein of certain avirulent NDV strains may differ from the genes encoding the HN proteins of more virulent strains of NDV by mutations generating a longer open reading frame and the consequent synthesis of a larger HN polypeptide.

Full length cDNA encoding the F and HN polypeptides

Full length copies of the coding regions of the F and HN genes were prepared as follows.

(1) F gene

The cDNA inserts from plasmids designated 3.01, 7.58 and 7.44 overlap and together cover the entire coding region of the NDV F gene. A full length copy of the coding region of the NDV F gene was inserted into the plasmid cloning vector pUC18 by ligating together restricted vector DNA (a) and each of restriction fragments (b), (c) and (d) described below in one simultaneous ligation. All DNA samples (a), (b), (c) and (d) were purified by electrophoresis on agarose gels, electroelution and phenol extractions as described by McDonnell et al., supra in connection with dot blot hybridisation. 2.5 units of calf intestinal alkaline phosphatase was present in each of the restrictions used to prepare fragments (b) and (d) below.

The restriction fragments used to construct a full length copy of the coding region of F gene were as follows:
(a) Cloning vector plasmid pUC18 restricted with enzymes BamHI and PstI, fragment size approximately 2.7 Kb.
(b) Plasmid 3.01 restricted with enzymes BamHI and SstI, fragment size approximately 0.6 Kb.
(c) Plasmid 7.58 restricted with enzymes SstI and AvaI, fragment size approximately 0.5 Kb.
(d) Plasmid 7.44 restricted with enzymes AvaI and PstI, fragment size approximately 1.25 Kb.

The PstI site referred to in (d) above is an artificial site created during the molecular cloning of NDV described above, and is linked by a poly (G,C) tract to the end of the cDNA insert of plasmid 7.44 at nucleotide 2514 in the DNA sequence given above. The BamHI, SstI and AvaI sites referred to in (b), (b) and (d) above occur at positions 17-22, 671-676 and 1258-1263 respectively in the DNA sequence given, and are indicated therein. Approximately 0.1 microgram of each of the restriction fragments (a), (b), (c) and (d) were ligated together in a single reaction for 2 hours at room temperature with T4 DNA ligase. The ligation mix was used to transform *E. coli* strain JM105, and recombinant plasmids (containing inserts) were selected as white colonies on ampicillin-Xgal indicator plates as described by U. Ruther, Mol. Gen. Genet. 178, 475-477 (1980). Plasmid insert sizes and the presence of appropriate restriction enzyme sites were verified on plasmid "minipreps". 10/11 plasmids screened contained full length copies of the NDV F gene.

(2) HN gene

The conditions used to construct a full length clone of the HN gene were as described above except that the restriction fragments (a), (b), (c) and (d) used were as described below:
(a) Cloning vector plasmid pUC19 restricted with enzymes SphI and SstI, fragment size approximately 2.7 Kb.
(b) Plasmid 7.44 restricted with enzymes SphI and NarI, fragment size approximately 0.8 Kb.
(c) Plasmid 4.68 restricted with enzymes NarI and AccI, fragment size approximately 0.45 Kb.
(d) Plasmid 1.13 restricted with enzymes AccI and SstI, fragment size approximately 0.87 Kb.

The restriction enzyme sites SphI, NarI, AccI and SstI referred to in (a), (b), (c) and (d) occur at positions 1610–1615, 2406–2411, 2860–2865 and 3733–3738 respectively in the DNA sequence given above.

In the case of the HN gene, 16 colonies were checked by plasmid "minipreps", one of which contained a full length copy of the HN gene.

The F gene cDNA (nucleotides 18–2514) cloned in pUC18 and HN gene cDNA (nucleotides 1615–3737) cloned in pUC19 and transformed into *E.coli* have been deposited as patent deposits under the provisions of the Budapest Treaty on the International Recognition of the Deposit of Microorganisms for the Purposes of Patent Procedure at the National Collection of Industrial Bacteria, Torry Research Station, P. O. Box 31, 135 Abbey Road, Aberdeen AB9 8DG, Scotland on Jul. 1st, 1986 under the numbers NCIB 12277 and 12278 respectively.

We claim:

1. DNA encoding a polypeptide bioprecursor of the HN glycoprotein of Newcastle Disease Virus.

2. DNA encoding a polypeptide bioprecursor of the HN glycoprotein of Newcastle Disease Virus and which hybridizes to a DNA encoding the polypeptide bioprecursor of the HN glycoprotein of the Beaudette C strain of Newcastle Disease Virus.

3. Recombinant DNA consisting of vector DNA and DNA foreign thereto, the foreign DNA encoding a polypeptide bioprecursor of the HN glycoprotein of Newcastle Disease Virus.

4. Recombinant DNA consisting of vector DNA and DNA foreign thereto, the foreign DNA encoding a polypeptide bioprecursor of the HN glycoprotein of Newcastle Disease Virus and which hybridizes to a DNA encoding the polypeptide bioprecursor of the HN glycoprotein of the Beaudette C strain of Newcastle Disease Virus.

5. A bacterial or lower eukaryotic cell transformed by a cloning or expression vector, said vector being composed of recombinant DNA consisting of vector DNA and DNA foreign thereto, the foreign DNA encoding a polypeptide bioprecursor of the HN glycoprotein of Newcastle Disease Virus.

6. A bacterial or lower eukaryotic cell transformed by a cloning or expression vector, said vector being composed of the recombinant DNA consisting of vector DNA and DNA foreign thereto, the foreign DNA encoding a polypeptide bioprecursor of the HN glycoprotein of Newcastle Disease Virus and which hybridizes to a DNA encoding the polypeptide bioprecursor of the HN glycoprotein of the Beaudette C strain of Newcastle Disease Virus.

7. DNA encoding a polypeptide bioprecursor of the F glycoprotein of Newcastle Disease Virus.

8. DNA encoding a polypeptide bioprecursor of the F glycoprotein of Newcastle Disease Virus and which hybridizes to a DNA encoding the polypeptide bioprecursor of the F glycoprotein of the Beaudette C strain of Newcastle Disease Virus.

9. Recombinant DNA consisting of vector DNA and DNA foreign thereto, the foreign DNA encoding a polypeptide bioprecursor of the F glycoprotein of Newcastle Disease Virus.

10. Recombinant DNA consisting of vector DNA and DNA foreign thereto, the foreign DNA encoding a polypeptide bioprecursor of the F glycoprotein of Newcastle Disease Virus and which hybridizes to a DNA encoding the polypeptide bioprecursor of the F glycoprotein of the Beaudette C strain of Newcastle Disease Virus.

11. A bacterial or lower eukaryotic cell transformed by a cloning or expression vector, said vector being composed of recombinant DNA consisting of vector DNA and DNA foreign thereto, the foreign DNA encoding a polypeptide bioprecursor of the F glycoprotein of Newcastle Disease Virus.

12. A bacterial or lower eukaryotic cell transformed by a cloning or expression vector, said vector being composed of the recombinant DNA consisting of vector DNA and DNA foreign thereto, the foreign DNA encoding a polypeptide bioprecursor of the F glycoprotein of Newcastle Disease Virus and which hybridizes to a DNA encoding the polypeptide bioprecursor of the F glycoprotein of the Beaudette C strain of Newcastle Disease Virus.

* * * * *